United States Patent [19]

Metcalf et al.

[11] 4,039,549
[45] Aug. 2, 1977

[54] OLEFINIC DERIVATIVES OF AMINO ACIDS

[75] Inventors: Brian Walter Metcalf, Strasbourg; Michel Jung, Illkirch, both of France

[73] Assignee: Merrell Toraude et Compagnie, Strasbourg, France

[21] Appl. No.: 664,991

[22] Filed: Mar. 8, 1976

Related U.S. Application Data

[62] Division of Ser. No. 559,544, March 18, 1975, Pat. No. 3,960,927.

[51] Int. Cl.$^2$ .............. C07D 211/76; C07D 207/26; C07C 103/183; C07C 103/28
[52] U.S. Cl. .............. 260/293.86; 260/326.5 FL; 260/561 A; 260/558 A; 260/559 A
[58] Field of Search .............. 260/293.86, 326.5 FL, 260/558 A, 559 A, 561 A

[56] References Cited

U.S. PATENT DOCUMENTS

| | | | |
|---|---|---|---|
| 2,447,587 | 8/1948 | Martin et al. | 260/559 A |
| 2,460,708 | 2/1949 | Mozingo et al. | 260/482 R |
| 2,531,595 | 11/1950 | Albertson | 260/534 R |
| 2,588,969 | 3/1952 | Dickey et al. | 260/482 R |
| 2,649,438 | 8/1953 | Bruson | 260/293.86 |
| 3,223,729 | 12/1965 | Gubitz | 260/534 R |
| 3,959,356 | 5/1976 | Metcalf et al. | 260/293.86 |
| 3,960,927 | 6/1976 | Metcalf et al. | 260/293.86 |

*Primary Examiner*—John M. Ford
*Attorney, Agent, or Firm*—L. Ruth Hattan; Eugene O. Retter; George W. Rauchfuss, Jr.

[57] ABSTRACT

Novel compounds of the following general formula are useful pharmacologic agents:

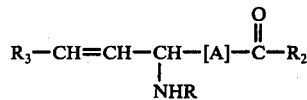

R is selected from hydrogen, alkylcarbonyl wherein the alkyl moiety contains from 1 to 4 carbon atoms, alkoxycarbonyl wherein the alkoxy moiety contains from 1 to 4 carbon atoms and may be a straight or branched, and

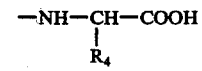

wherein $R_{10}$ is selected from hydrogen, a straight or branched lower alkyl group of from 1 to 4 carbon atoms, benzyl and p-hydroxybenzyl; $R_2$ is selected from hydroxy, a straight or branched alkoxy group of from 1 to 8 carbon atoms, a lower alkylamino group wherein the alkyl moiety contains from 1 to 4 carbon atoms, and

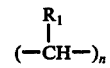

wherein $R_4$ is selected from hydrogen, a straight or branched lower alkyl group of from 1 to 4 carbon atoms, benzyl, and p-hydroxybenzyl; $R_3$ is selected from hydrogen, chlorine, bromine, and iodine; [A] is selected from

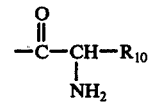

and —CH=CH— wherein $R_1$ is selected from hydrogen, lower alkyl of from 1 to 4 carbon atoms, phenyl and substituted phenyl wherein the substituents on the substituted phenyl may be attached at the ortho, meta or para positions of the phenyl ring and are selected from halogen, lower alkoxy of from 1 to 4 carbon atoms, and lower alkyl of from 1 to 4 carbon atoms; $n$ is an integer of from 1 to 5; and the lactams of said compounds wherein [A] represents

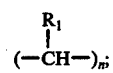

R and $R_1$ represent hydrogen and $n$ is the integer 2 or 3 and pharmaceutically acceptable salts and individual optical isomers thereof.

6 Claims, No Drawings

OLEFINIC DERIVATIVES OF AMINO ACIDS

This is a division, of application Ser. No. 559,544, filed Mar. 18, 1975 now U.S. Pat. No. 3,960,927 issued June 1, 1976.

BACKGROUND OF THE INVENTION

Several previous studies have shown that γ-aminobutyric acid is a major inhibitory transmitter of the central nervous system as reported, for example, by Y. Godin et al., Journal Neurochemistry, 16, 869 (1969) and that disturbance of the excitation and inhibition interplay can lead to diseased states such as Huntington's chorea, (The Lancet, Nov. 9, 1974, pp. 1122–1123), Parkinsonism, schizophrenia, epilepsy, depression, hyperkinesis and manic depression disorders [Biochem. Pharmacol. 23, 2637–2649 (1974)]. Certain compounds known to elevate brain levels of γ-aminobutyric acid, for example, n-dipropylacetate [Simler et al., Biochem. Pharm. 22, 1701 (1973)] by competitively inhibiting γ-aminobutyric acid transaminase result in a reversible effect which lasts for only about 2 hours. Also, 4-aminotetrolic acid [P.M. Beart et al., J. Neurochem. 19, 1849 (1972)] is known to be a competitive reversible inhibitor of γ-aminobutyric acid transaminase. We have now made the unexpected finding that compounds of our invention are able to irreversibly inhibit γ-aminobutyric acid transaminase and increase significantly the brain level of γ-aminobutyric acid in animals rendering them useful in the treatment of the aforementioned diseased states. Furthermore, this increase is long lasting (over 24 hours) and therefore, compounds of the present invention are not only structurally novel but are quite different in their properties from known compounds which elevate brain levels of γ-aminobutyric acid only for a short period of time.

SUMMARY OF THE INVENTION

The compounds of the present invention may be represented by the following general Formula I:

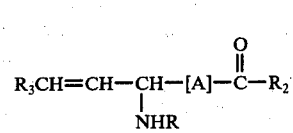

Formula I wherein R is selected from hydrogen, alkylcarbonyl wherein the alkyl moiety contains from 1 to 4 carbon atoms, alkoxycarbonyl wherein the alkoxy moiety contains from 1 to 4 carbon atoms and may be straight or branched, and

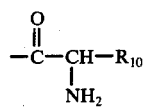

wherein $R_{10}$ is selected from hydrogen, a straight or branched lower alkyl group of from 1 to 4 carbon atoms, benzyl and p-hydroxybenzyl; $R_2$ is selected from hydroxy, a straight or branched alkoxy group of from 1 to 8 carbon atoms, a lower alkylamino group wherein the alkyl moiety contains from 1 to 4 carbon atoms and

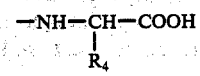

wherein $R_4$ is selected from hydrogen, a straight or branched lower alkyl group of from 1 to 4 carbon atoms, benzyl, and p-hydroxybenzyl; $R_3$ is selected from hydrogen, chlorine, bromine and iodine; [A] is selected from

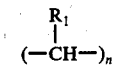

and —CH=CH— wherein $R_1$ is selected from hydrogen, lower alkyl of from 1 to 4 carbon atoms, phenyl and substituted phenyl wherein the substituents on the substituted phenyl may be attached at the ortho, meta or para positions of the phenyl ring and are selected from halogen, lower alkoxy of from 1 to 4 carbon atoms, and lower alkyl of from 1 to 4 carbon atoms; $n$ is an integer of from 1 to 5; and the lactams of said compounds wherein [A] represents

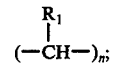

R and $R_1$ represent hydrogen and $n$ is the integer 2 or 3; and pharmaceutically acceptable salts and individual optical isomers thereof.

The compounds of general Formula I are useful as sedatives. The compounds of general Formula I wherein [A] represents —CH=CH— and

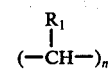

wherein $R_1$ is hydrogen, and $n$ is an integer of from 1 to 5, that is, compounds of the following general Formula II and the lactams of the compounds of Formula II wherein [A'] represents $(—CH_2—)_n$ and $n$ is the integer 2 or 3, as represented by the following Formula III, are useful as inhibitors of γ-aminobutyric acid transaminase resulting in an increase in brain levels of γ-aminobutyric acid rendering the compounds useful in the treatment of disorders of the central nervous system function consisting of involuntary movement associated with Huntington's chorea, Parkinsonism, extrapyramidal effects of drugs, for example, neuroleptics, seizure disorders associated with epilepsy, alcohol withdrawal, barbiturate withdrawal, psychoses associated with schizophrenia, depression, manic depression, and hyperkinesis. Compounds of this invention are also useful as hypothermic agents, myorelaxants, cholinergic agents, antibacterial agents, anticonvulsant agents, analgesics, anorexigenic agents, antiobesity agents, tranquillizers, sedatives and central nervous system stimulants.

Formula II

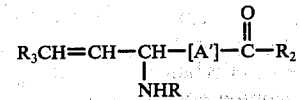

In the above general Formula II, the substituent groups R, $R_2$ and $R_3$ have the meanings defined in general Formula I and [A'] is selected from —CH=CH— and (—CH$_2$—)$_n$ wherein $n$ is an integer of from 1 to 5; and pharmaceutically acceptable salts and individual optical isomers

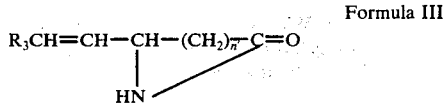

Formula III

In the above Formula III n' is the integer 2 or 3; R$_3$ has the meaning defined in Formula I; and pharmaceutically acceptable salts and individual optical isomers thereof.

DETAILED DESCRIPTION OF INVENTION

As used herein, the term lower alkylcarbonyl means the substituent group

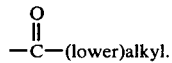

As used herein, the term alkoxycarbonyl means the substituent group

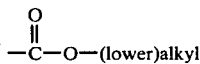

wherein the lower alkyl moiety may be straight or branched.

Illustrative examples of straight chain lower alkyl groups of from 1 to 4 carbon atoms referred to herein are methyl, ethyl, n-propyl and n-butyl, and of branched chain lower alkyl groups of from 1 to 4 carbon atoms are isopropyl, isobutyl and tert-butyl.

Illustrative examples of straight chain lower alkoxy groups of from 1 to 4 carbon atoms as used herein are methoxy, ethoxy, n-propoxy and n-butoxy, and of branched chain lower alkoxy groups of from 1 to 4 carbon atoms are isopropoxy, isobutoxy, and tert-butoxy.

Illustrative examples of straight or branched alkoxy groups of from 1 to 8 carbon atoms as used herein are methoxy, ethoxy, n-propoxy, isopropoxy, n-butoxy, tert-butoxy, neo-pentoxy, pentoxy, octyloxy, heptyloxy and hexyloxy.

Illustrative examples of lower alkylamino groups which R$_2$ may represent are methylamino, ethylamino, n-propylamino, and n-butylamino.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids such as methane sulfonic, salicylic, maleic, malonic, tartaric, citric, and ascorbic acids; and non-toxic salts formed with inorganic or organic bases such as those of alkali metals, for example, sodium, potassium and lithium, alkaline earth metals, for example, calcium and magnesium, light metals of Group III A for example, aluminum; organic amines such as primary, secondary or tertiary amines, for example, cyclohexylamine, ethylamine, pyridine, methylaminoethanol, ethanolamine and piperazine. The salts can be prepared by conventional means.

The compounds of this invention where [A] represents the group

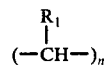

can be represented by the following Formula IV:

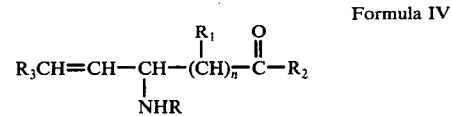

Formula IV wherein the substituents R, R$_1$, R$_2$, R$_3$ and $n$ have the meanings defined in general Formula I.

The compounds of this invention wherein [A] represents —CH=CH— can be represented by the following Formula V:

$$R_3CH=CH-CH-CH=CH-\overset{\overset{O}{\|}}{C}-R_2$$
$$\underset{NHR}{|}$$

Formula V wherein the substituents R, R$_2$ and R$_3$ have the meanings defined in general Formula I.

The lactams which are included within the scope of this invention are represented by the compounds of general Formula III described hereinabove.

Illustrative examples of compounds of this invention are the following:
3-amino-4-ene-pentanoic acid,
4-amino-5-ene-hexanoic acid,
7-amino-8-ene-nonanoic acid,
6-amino-3-ethyl-7-ene-octanoic acid,
4-amino-2-(p-anisyl)-5-ene-hexanoic acid,
5-amino-3-(p-anisyl)-6-ene-heptanoic acid,
N-methyl-(2-amino-3-ene-butan-1-yl)carboxamide,
4-amino-6-chloro-5-ene-hexanoic acid,
4-amino-3-phenyl-5-ene-hexanoic acid,
4-amino-5-ene-1-oxo-hexan-1-ylaminoacetic acid,
5-methoxycarbonylamino-6-ene-heptanoic acid,
4-acetylamino-5-ene-hexanoic acid,
3-amino-4-ene-pentanoic acid methyl ester, and
4-amino-2-ene-5-ene-hexanoic acid.

Preferred compounds of this invention are those of general Formula II. More preferred compounds of this invention are those of general Formula II wherein the substituent group R$_2$ is hydroxy or alkoxy. Still more preferred compounds of this invention are those of general Formula II wherein the substituent group R$_2$ is hydroxy, and $n$ is the integer 1 or 2. An even more preferred group of compounds of this invention are those of general Formula II wherein the substituent group R$_2$ is hydroxy, $n$ is an integer of 1 or 2 and each of R and R$_3$ is hydrogen. Of the preferred compounds of this invention, the (+) isomers are the most preferred compounds.

The compounds of this invention have a variety of pharmacological utilities. The compounds of this invention are useful as sedatives. The compounds of general Formulas II and III are useful as inhibitors of γ-aminobutyric acid transaminase resulting in an increase in brain levels of γ-aminobutyric acid rendering the compounds useful in the treatment of disorders of the central nervous system function consisting of involuntary movement associated with Huntington's chorea, Parkinsonism, extrapyramidal effects of drugs, for example, neuroleptics, seizure disorders associated with epilepsy, alcohol withdrawal, and barbiturate withdrawal, psychoses associated with schizophrenia, depression and manic depression and hyperkineses. Compounds of this invention are also useful as hypothermic agents, myorelaxants, cholinergic agents, antibacterial agents, anticonvulsant agents, analgesics, anorexigenic agents, antiobesity agents, tranquilizers, sedatives, and central nervous system stimulants.

The sedative properties of the compounds of this invention were determined by measuring spontaneous motor activity in rodents by the procedure described by P. Dews, Brit. J. Pharmacol. 8, 46 (1953).

The ability of the compounds of general Formulas II and III to inhibit γ-aminobutyric acid transaminase is determined in vitro and in vivo by measuring γ-aminobutyric acid transaminase activity. γ-Aminobutyric acid levels are markedly increased in mice and rat brains after treatment with compounds of general Formula II at doses between 25–200 mg/kg by parenteral and oral routes. This ability is further shown by the protective effect of this treatment on audiogenic seizures in mice of the DBA strain measured by the general method described by Simler et al., Biochem. Pharamacol. 22, 1701 (1973), which is currently used to evidence anti-epileptic activity.

The ability of the compounds of this invention, at doses ranging from 50 to 200 mg/kg, to alleviate reserpine ptosis has been shown by the classical test of B. Rubin et al., J. Pharmacol. 120, 125 (1957), which is currently used to determine anti-depressant activity.

The ability of the compounds of this invention to promote loss of body weight in rats has been demonstrated by weighing animals which were given daily doses ranging from 10–50 mg/kg of these compounds.

The compounds of this invention can be administered orally or parenterally to animals, particularly warm blooded animals and mammals and humans either alone or in the form of pharmaceutical preparations containing as the active ingredient compounds of this invention to achieve the desired effect. Pharmaceutical preparations containing compounds of this invention and conventional pharmaceutical carriers can be employed in unit dosage forms such as solids, for example, tablets, pills and capsules or liquid solutions, suspensions or elixirs for oral administration or liquid solutions, suspensions and emulsions for parenteral use. The quantity of compounds administered can vary over a wide range to provide from about 0.1 mg/kg to about 300 mg/kg of body weight of the patient per day. Unit doses of these compounds can contain, for example, from about 50 mg to 2000 mg of the compounds and may be administered, for example, from 1 to 4 times daily. Following are illustrative examples of pharmaceutical preparations containing the compounds of this invention.

|     |                          | Per tablet |
| --- | ------------------------ | ---------- |
| (a) | 3-amino-4-ene-pentanoic acid | 100.0 mg |
| (b) | wheat starch             | 15.0 mg    |
| (c) | lactose                  | 33.5 mg    |
| (d) | magnesium stearate       | 1.5 mg     |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following wherein the quantities are on a weight to volume basis:

|     |                          | Amount    |
| --- | ------------------------ | --------- |
| (a) | (+)4-amino-5-ene-hexanoic acid | 100.0 mg |
| (b) | sodium chloride          | q.s.      |
| (c) | water for injection to make | 20 ml  |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

An illustrative composition for hard gelatin capsules is as follows:

|     |                          | Amount    |
| --- | ------------------------ | --------- |
| (a) | 3-amino-4-ene-pentanoic acid | 200.0 mg |
| (b) | talc                     | 35.0 mg   |

The composition is prepared by passing the dry powders of (a) and (b) through a fine mesh screen and mixing them well. The powder is then filled into No. 0 hard gelatin capsules at a net fill of 235 mg per capsule.

The compounds of general Formula I wherein $R_2$ is other than

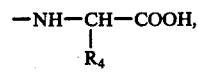

and R is hydrogen are prepared by catalytic or organic semi-hydrogenation of the corresponding acetylene derivative which may be represented by the following Formula VI:

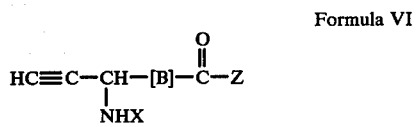

Formula VI wherein X is alkylcarbonyl or hydrogen wherein the alkyl moiety contains from 1 to 4 carbons atoms; Z is selected from hydroxy or a straight or branched alkoxy group of from 1 to 8 carbon atoms; and [B] is selected from —CH=CH— and

wherein Q is selected from hydrogen, lower alkyl of from 1 to 4 carbon atoms, phenyl, and substituted phenyl wherein the substituents on the substituted phenyl may be attached at the ortho, meta or para positions of the phenyl ring and are selected from halogen, lower alkoxy of from 1 to 4 carbon atoms, and lower alkyl of from 1 to 4 carbon atoms; and p is an integer of from 1 to 5.

Catalytic hydrogenation can be carried out in the presence of a base, for example, pyridine or triethylamine using inorganic catalysts as described by E. N.

Marvell and T. Li, Synthesis, No. 8, Aug., 1973 pp. 457–468, for example, palladium-on-barium sulfate or the Lindlar catalyst, that is, lead-poisoned palladium-on-calcium carbonate. The hydrogenation process is continued until there is a reduction in the uptake of hydrogen.

The organic hydrogenation is achieved by reacting equimolar amounts of a compound of Formula I and catecholborane under a nitrogen atmosphere at about 70° C for about 2 hours by the general procedures described by H. C. Brown and S. K. Gupta, J. Am. Chem. Soc. 94, 4370–4371 (1972), H. C. Brown et al., J. Am. Chem. Soc. 95, 5786–5788 and 6456–6457 (1973). The specific examples below are illustrative of the preparation of the compounds of this invention.

The compounds of general Formula VI wherein X is hydrogen are prepared by reacting a suitably protected propargylamine derivative as represented by compound I below with an alkylating reagent in the presence of a base and subsequently unmasking the protecting groups by treatment with acid or base as represented by the following reaction:

Formula VI

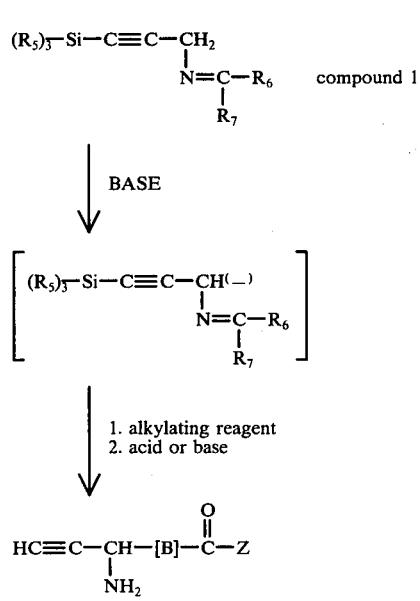

In the above reaction sequence, [B] and Z have the meanings defined in general Formula VI; $R_5$ is selected from a lower alkyl group having from 1 to 4 carbon atoms such as methyl, ethyl and n-propyl; $R_6$ is selected from hydrogen or phenyl; and $R_7$ is selected from phenyl or trialkylmethyl.

In the above reaction, the protected propargylamine derivative compound 1, is treated with a strong base to form the carbanion intermediate. Suitable strong bases are those which will abstract a proton from the carbon adjacent to the acetylene moiety, such as, alkyl lithium, for example, butyl lithium, or phenyl lithium, lithium di-alkylamide, for example, lithium diisopropylamide, lithium amide, tertiary potassium butylate, sodium amide and sodium hydroxide.

Following addition of the base the alkylating reagent is added. The alkylating reagents employed in the above reaction are selected from derivatives having the structures:

(A) when [B] is $-(CH)_p^-$ and p is equal to 2,

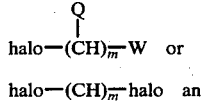

(B) when [B] is $-(CH)_p^-$ and p is equal to 1 or 3 to 5, $$halo-(CH)_m^-W \quad or$$

$$halo-(CH)_m^-halo \quad and$$

C. when [B] is $-CH=CH-$, $haloCH=CHCOR_2$, or $HC\equiv C-COR_9$ wherein Q has the meaning defined in general Formula VI; W is selected from cyano or

wherein $R_9$ is a straight or branched alkoxy group of from 1 to 8 carbon atoms; m is the integer 1 or 3 to 5; and halo is iodine, bromine or chlorine.

When the alkylating reagent employed is the dihaloalkyl derivative as set forth in (B), subsequent to the alkylation reaction the ω-halogen is displaced with cyanide, and as when W is cyano the reaction mixture is treated with an acid or base to hydrolyze the nitrile to the corresponding acid or amide derivative as represented by Formula I by procedures well known in the art. Similarly, the protecting groups that is, the acetylene and the amino protecting groups and the ester or amide functions if desired can be removed with aqueous acid, for example, hydrochloric or toluene sulfonic acid or aqueous base, for example, sodium hydroxide or potassium hydroxide. The amino protecting groups can also be removed by using hydrazine or phenylhydrazine.

The alkylation reaction is carried out in an aprotic solvent for example, benzene, toluene, ethers, tetrahydrofuran, dimethylsulfoxide, dimethyl formamide, dimethyl acetamide, hexamethyl phosphoramide and hexamethyl phosphortriamide. The reaction temperature varies from −120° C to room temperature, and a preferred reaction temperature is about −70° C. The reaction time varies from ½ hour to 24 hours. The protected propargylamine derivatives, compound 1, are prepared by the addition of protecting groups on the acetylene function and the nitrogen function of propargylamine. Protection of nitrogen function of propargylamine is accomplished by forming in a known manner, a Schiff's base with a non-enolizable carbonyl bearing compound, such as benzaldehyde, benzophenone, or trialkylacetaldehyde. Protection of the acetylenic function is accomplished by reacting the above described Schiff's base with trimethylsilylchloride, triethylsilylchloride or high trialkylsilylchloride forming in a known manner (E. J. Corey and H. A. Kirst, Tetrahedron Letters, 1968, 5041) the corresponding trialkylsilyl derivatives.

The alkylating reagents employed in the above reaction are known in the art or can be prepared by procedures wellknown in the art.

Compounds of Formula VI wherein X is alkylcarbonyl are prepared from the corresponding derivative wherein X is hydrogen using an appropriate acid anhydride, or halide of acetic, propionic, butyric or valeric acids.

Compounds of this invention where R is alkylcarbonyl are prepared from the corresponding acid wherein R represents hydrogen using the appropriate acid anhydride or halide of acetic acid, propionic acid, butyric acid or valeric acid. The amide derivatives of this invention can be isolated as the acid or a derivative thereof, for example, the ester by converting the acid to the acid halide, for example, by treating with thionyl chloride followed by alcoholysis, to get the appropriate ester by procedure generally known in the art.

Compounds of general Formula I wherein R is alkoxycarbonyl are prepared from the corresponding acid wherein R represents hydrogen using an appropriate alkyl chloroformate for example, methyl chloroformate, ethyl chloroformate, n-propyl chloroformate, n-butyl chloroformate, isobutyl chloroformate or tert-butyl chloroformate in the presence of a base by procedures well known in the art.

Compounds of general Formula I wherein R is

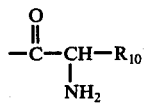

are prepared by treating an ester of a compound of Formula I wherein R is hydrogen with a protected acid of the formula HOOC-CH(NH$_2$)-R$_{10}$ wherein the amino function is protected with a suitable blocking group, such as, benzyloxycarbonyl or tert-butoxycarbonyl. Either the free acid or a reactive derivative thereof, for example, an acid anhydride may be employed. When the free acid is used, a dehydrating agent such as N,N'-dicyclohexylcarbodiimide is used. The substituent R$_{10}$ has the meaning defined in general Formula I.

Compounds of this invention wherein R$_2$ represents

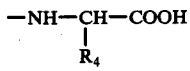

are prepared from the corresponding acid derivative wherein the amino function is protected with a suitable blocking group, such as benzyloxycarbonyl or tert-butoxycarbonyl. The amino protected derivatives either as the free acid, in which case a dehydrating agent such as N,N'-dicyclohexylcarbodiimide is used, or a reactive derivative of the acid, such as, an acid anhydride, is reacted with a compound of the structure

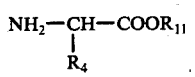

wherein R$_4$ has the meaning defined in general Formula I, and R$_{11}$ is a lower alkyl group, for example, methyl or ethyl, followed by base hydrolysis to remove the protecting group by procedures well known in the art.

The lactams of this invention as described by general Formula III are prepared from the corresponding amino acid, that is, a compound of the formula:

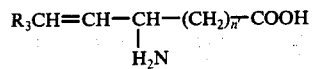

or ester thereof wherein n' is the integer 2 or 3, and R$_3$ is hydrogen, chlorine, bromine or iodine, by procedures generally known in the art, for example, by treating the amino acid with a dehydrating agent such as dicyclohexylcarbodiimide or by heating the appropriate ester derivative.

The optical isomers of the compound of this invention may be separated by using a (+) or (−) binaphthylphosphoric acid derivative or a salt of said derivative and an optically active base by the method described by R. Viterbo, et al., in *Tetrahedron Letters*, 48, 4617–4620 (1971) and in U.S. Pat. No. 3,848,030.

EXAMPLE 1

4-AMINO-5-ENE-HEXANOIC ACID

A. To a solution of 183 mg (1 mm) of 4-acetamido-5-ynehexanoic acid methyl ester in 10 ml of chloroform was added 20 mg of Lindlar catalyst (5% Pd/CaCO$_3$/PbO$_2$). The suspension was stirred under hydrogen and the hydrogen absorption recorded. After 12 hours, the hydrogen absorption equaled 22 ml and the reaction was stopped by nitrogen flushing. After filtration of the catalyst the solution is concentrated and 4-acetamido-5-ene-hexanoic acid methyl ester is separated by dry column chromatography on silica gel using ethyl acetate as the eluant. The oil product thus obtained is hydrolized in hot 6 N HCl(20 ml, 12 hours reflux). The aqueous solution is evaporated under vacuum after ether extraction, and the syrup taken up in 2 ml of water. The product is isolated by ion exchange chromatography on an acid resin.

Alternatively, 4-amino-5-ene-hexanoic acid may be prepared by the following procedures:

B. A mixture of 130 mg (1 mM) of 4-amino-5-yne-hexanoic acid in 10 ml of water containing 1 ml of pyridine and Lindlar catalyst was stirred under a hydrogen atmosphere. Hydrogen uptake ceased at 24 ml. The mixture was filtered, the solvents evaporated under reduced pressue and the residue recrystallized from ethanol-water to afford the product.

C. A mixture of 300 mg (2 mM) of 4-acetamido-5-ynehexanoic acid methyl ester and 240 mg (2 mM) of catecholborane was stirred under nitrogen atmosphere at 70° C for 2 hours. After being cooled to room temperature, 5 ml of acetic acid was added and the mixture was heated at 70° C for 4 hours after which 30 ml of 6 N HCl was added. The mixture was refluxed overnight, and on cooling, the aqueous solution was washed with methylene chloride, adjusted to a pH of 8 and reextracted with methylene chloride. The aqueous base was adjusted to a pH of 6. The product was isolated by ion exchange chromatography on an acid resin followed by recrystallization from ethanol.

EXAMPLE 2

4-AMINO-6-IODO-5-ENE-HEXANOIC ACID

A mixture of 300 mg (2 mM) of 4-acetamido-5-ynehexanoic acid methyl ester and 240 mg (2 mM) of catecholborane was stirred under a nitrogen atmosphere at 70° C for 2 hours. Upon cooling to room temperature, the mixture was stirred with 50 ml of water for 2 hours at 25° C. On cooling to 0° C, a solid separated which was filtered off, then dissolved in 30 ml of ether and cooled to 0° C. Aqueous NaOH (5 ml, 3 N), was added followed by iodine (2 mM) in 20 ml of ether. After one-half hour, aqueous thiosulfate solution was added.

The aqueous layer was separated and concentrated. The residue was treated with 6 N HCl (30 ml) at 100° C for 6 hours and the product was isolated by ion exchange chromatography.

EXAMPLE 3

4-AMINO-6-BROMO-5-ENE-HEXANOIC ACID

A mixture of 300 mg (2 mM) of 4-acetamido-5-ene-hexanoic acid methyl ester and 240 mg (2 mM) of catecholborane was stirred under a nitrogen atmosphere for 2 hours. Upon cooling to room temperature, the reaction product was dissolved in 30 ml of methylene chloride and cooled to 0° C after which 640 mg (4 mM) of bromine was added. After another hour, water was added and the organic phase separated, dried over magnesium sulfate and evaporated. The residue was refluxed overnight in 30 ml of 6 N HCl and the product isolated by ion exchange chromatography using an acid resin.

EXAMPLE 4

Following the procedure of Example 1 (A), (B) or (C) only substituting for 4-acetamido-5-yne-hexanoic acid methyl ester an appropriate amount of 3-amino-4-yne-pentanoic acid, 5-amino-6-yne-heptanoic acid, 4-amino-3-phenyl-5-yne-hexanoic acid, or 4-amino-5-yne-2-ene-hexanoic acid, or an acetamido-ester derivative thereof, obtained by conventional methods, the following respective products are obtained: 3-amino-4-ene-pentanoic acid, 5-amino-6-ene-heptanoic acid, 4-amino-3-phenyl-5-ene-hexanoic acid, and 4-amino-2,5-dienehexanoic acid.

EXAMPLE 5

4-(2-AMINOPROPRIONAMIDO)-5-ENE-HEXANOIC ACID

4-Amino-5-ene-hexanoic acid methyl ester is prepared by refluxing a suspension of 1.27 g of 4-amino-5-ene-hexanoic acid in 20 ml of methanol with continuous anhydrous HCl bubbling through the reaction mixture for 3 hours followed by evaporation of the solvent, dissolution in water, neutralization with aqueous NaOH in the cold and ether extraction. The ether solution is dried over magnesium sulfate, filtered, and cooled to 0° C. Under moisture exclusion a solution of 10 mMoles of α-alanine, wherein the amino function is protected with benzyloxycarbonyl and the acid function is activated with ethoxycarbonyl, prepared by the methods known in the art, in ether is added slowly with stirring. When addition is complete the cooling bath is removed and stirring continued overnight. The solution is evaporated leaving a syrupy residue which is taken up in 2 ml of methanol and 10 ml of 2 N aqueous ammonia added. The suspension is stirred at 50° C for 1 day then extracted with ether. The product is isolated by ion exchange chromatography on an acid resin.

EXAMPLE 6

N-(2-PROPIONIC ACID)-3-AMINO-4-ENE-PENTAN-1-YL CARBOXAMIDE

To a solution of 1.27 g of 4-amino-5-ene-hexanoic acid (10 mM) in 10 ml of water was added 10.0 ml of 2 N NaOH. This solution was cooled in ice water and 1.87 g (11 mM) of benzylchloroformate was added slowly with stirring. When the addition was complete, stirring is continued for 1 hour. The solution is acidified to a pH of 4 by addition of aqueous HCl and the oily precipitate is extracted into ether. The ether solution is dried over magnesium sulfate, filtered and cooled. After addition of 700 mg of triethylamine, an ethereal solution of 11 g of freshly distilled ethylchloroformate is added slowly over 1 hour with stirring. The precipitate is filtered off and to the ether solution a solution of alanine methyl ester in ether is added at once. The solution is kept overnight and then evaporated to dryness. The residue is taken up in 2 ml of methanol and 20 ml of 2 N aqueous NaOH is added. The suspension is stirred for 1 day at 50° C then the solution is extracted with ether and adjusted to a pH of 7. The product is isolated by ion exchange chromatography on an acid resin.

We claim:
1. A compound of the formula:

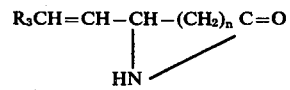

wherein n' is the integer 2 or 3; and $R_3$ is hydrogen, chlorine, bromine or iodine; or a pharmaceutically useful salt and individual optical isomers thereof.

2. A compound of the formula

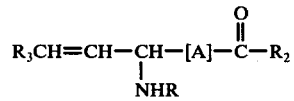

wherein R is hydrogen, alkylcarbonyl wherein the alkyl moiety contains from 1 to 4 carbon atoms, or

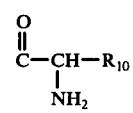

wherein $R_{10}$ is hydrogen, a straight or branched lower alkyl group of from 1 to 4 carbon atoms, benzyl, or p-hydroxybenzyl; $R_2$ is a lower alkyl amino group wherein the alkyl moiety has from 1 to 4 carbon atoms; $R_3$ is hydrogen, chlorine, bromine or iodine; [A] is —CH=CH— or

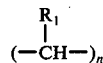

wherein $R_1$ is hydrogen, lower alkyl of from 1 to 4 carbn atoms, phenyl or substituted phenyl wherein the substituents on the substituted phenyl may be attached at the ortho, meta or para positions of the phenyl ring and are halogen, lower alkoxy of from 1 to 4 carbon atoms or lower alkyl of from 1 to 4 carbon atoms; n is an integer of from 1 to 5; and the lactams of said compounds wherein [A] represents

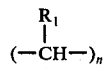

wherein $R_1$ represents hydrogen, and n is the integer 2 or 3; or a pharmaceutically acceptable salt and individual optical isomers thereof.

3. A compound of claim 2 of the formula:

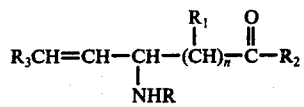
wherein R, $R_1$, $R_2$, $R_3$ and n have the meanings defined in claim 9.
4. A compound of claim 3 wherein $n$ is the integer 1 or 2.
5. A compound of claim 4 wherein R is hydrogen.
6. A compound of claim 2 of the formula:
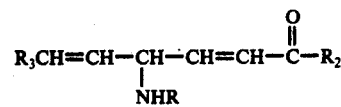
wherein R, $R_2$ and $R_3$ have the meanings defined in claim 9.
* * * * *

UNITED STATES PATENT AND TRADEMARK OFFICE
CERTIFICATE OF CORRECTION

PATENT NO. : 4,039,549
DATED : August 2, 1977
INVENTOR(S) : Brian W. Metcalf and Michel Jung It is certified that error appears in the above-identified patent and that said Letters Patent are hereby corrected as shown below:

On the cover sheet, in the Abstract, at line 1, column 2, the patent reads "may be a straight or" and should read --may be straight or--
At column 8, line 66, the patent reads "wellknown" and should read --well-known--
At column 10, line 40, the patent reads "pressue" and should read --pressure--. At column 12, claim 1, line 17, the structure reads $$R_3CH=CH-CH-(CH_2)_nC=O$$
$$\phantom{R_3CH=CH-CH-}|\phantom{(CH_2)_nC=O}$$
$$\phantom{R_3CH=CH-CH-(CH_2)_nC=}HN$$

and should read $$R_3CH=CH-CH-(CH_2)_{n'}C=O$$
$$\phantom{R_3CH=CH-CH-}|$$
$$\phantom{R_3CH=}HN$$

At column 12, in claim 2, line 51, the patent reads "carbn" and should read --carbon--. At column 13, claim 3, line 9, the patent reads "in claim 9" and should read --in claim 2--. At column 14, in claim 6, line 10, the patent reads "in claim 9" and should read --in claim 2--.

Signed and Sealed this

Twenty-seventh Day of November, 1990

*Attest:*

HARRY F. MANBECK, JR.

*Attesting Officer*   *Commissioner of Patents and Trademarks*